United States Patent [19]

Sakamoto et al.

[11] 4,288,162

[45] Sep. 8, 1981

[54] MEASURING PARTICLE SIZE DISTRIBUTION

[75] Inventors: Yoshiyasu Sakamoto; Yoichi Tamura; Kiyohiko Kawaguchi; Kiyotaka Inada, all of Amagasaki, Japan

[73] Assignee: Sumitomo Kinzoku Kogyo Kabushiki Kaisha, Osaka, Japan

[21] Appl. No.: 15,871

[22] Filed: Feb. 27, 1979

[51] Int. Cl.³ .......................................... G01N 15/02
[52] U.S. Cl. .................................................. 356/335
[58] Field of Search ...................... 356/335, 439, 380; 250/222 PC, 573

[56] References Cited

U.S. PATENT DOCUMENTS

| | | | |
|---|---|---|---|
| 3,275,744 | 9/1966 | Dietrich | 250/222 PC |
| 3,641,320 | 2/1972 | Stockham et al. | 356/335 |

*Primary Examiner*—John K. Corbin
*Assistant Examiner*—Bruce Y. Arnold
*Attorney, Agent, or Firm*—Wenderoth, Lind & Ponack

[57] ABSTRACT

A method and apparatus for determining the particle size distribution of particles in a mass of a granular substance. The particles are caused to fall in a stream of separate particles past an irradiated screen, and an instantaneous television picture is taken of the particles and the projected images of the particles are used to measure the projected areas of the particles. Using these areas assuming the average shape of the particles to be substantially a rotational ellipsoid and using a coefficient according to the average configuration of the particles, the particle sizes and their distribution in the mass of particles are calculated.

6 Claims, 9 Drawing Figures

MEASURING PARTICLE SIZE DISTRIBUTION

BACKGROUND OF THE INVENTION

1. Field of the Invention

The present invention relates to a method for measuring particle size distribution in masses of granular substances, such as various raw materials for making iron, cereals, etc., and more particularly to a method of measuring particle size distribution continuously during transportation of the particles. The invention also relates to an apparatus to carry out particle size measurement according to the method.

2. Description of the Prior Art

As is well-known, it is important to know the particle size distribution in various raw materials to be charged into a blast furnace just before they are charged in order to stabilize the operating conditions of the furnace, because the particle size distribution in the raw materials plays an important role on the permeability of air through the furnace. Furthermore, is is necessary for judging the quality of cereals to know the particle size distribution.

The measurement of the particle size distribution of masses of granular substances has, hitherto, been done in a way exemplified by how measurement has been carried out on the raw materials used for iron making. Midway along a conveyor belt for transporting these materials is provided a sampling device, and samples are taken from the raw material which is being conveyed on the conveyor belt continuously one by one at appropriate time intervals. Each sample is divided into 4 to 5 fractions using sieves and the weight of each fraction is measured by a weighing device. The particle size distribution of the raw material is then determined from the relative weight of each fraction of the sample in relation to the whole sample. This method of measurement has several disadvantages. Both the sampling device and the weighing device must be large, because it is necessary to make each sample large in order to make the results accurate and useful for the large amount of raw material consumed in a blast furnace. Further, the time interval for sampling, or in other words, the sampling period, is usually rather long, such as 30 minutes to 1 hour, due to the fact that the time necessary for the dividing up of a sample is rather long.

This method makes the validity of each sample for the total amount of material used in a furnace uncertain, and it has thus been difficult to get reliable data on the particle size distribution by this prior art method. Moreover, since it takes more than 1 hour to determine the size distribution of a sample after taking it from raw material being conveyed, any proper feedback of these results, to adjust the particle size distribution, is too late to properly adjust the particle size distribution effectively. This is a serious disadvantage of the prior art method.

OBJECTS AND BRIEF SUMMARY OF THE INVENTION

One object of the present invention is to provide a method of measuring particle size distribution of masses of substances which does not require taking any sample from the masses and which is, accordingly, possible to carry out continuously.

Another object of the invention is to provide a method of measuring particle size distribution which makes it possible to obtain a very accurate determination of the particle size distribution rapidly and thus to use the obtained distribution as information for feedback control for the particle size regulation.

A further object of the invention is to provide a method of measuring particle size distribution which is not limited to any range of particle size distribution or to a particular number of fractions.

A still further object of the invention is to provide a method of measuring particle size distribution which gives a result which corresponds to the results obtained by the prior art method using sieves even if the configuration of each particle in the mass of particles is irregular.

Another object of the invention is to provide an apparatus which can carry out said method of measuring particle size distribution and by the use of which it is possible to measure the particle size distribution of masses of granular substances even though the apparatus has a rather simple construction.

The objects are achieved by the method of measuring particle size distribution according to which a technique of data processing of information from projected images is utilized in order to overcome the disadvantages of the prior art as described. The objects are further achieved by an apparatus to carry out this method.

Compared with the prior art the characteristic feature of the present invention is that the method of the present invention carries out the measurement particle size distribution of masses of granular substances by processing static images of particles of the mass projected statically when the mass is falling in a stream with a definite vertical fall.

Moreover, the invention also includes a method of correcting the particle size distribution which can be used during a measurement, by using an average configuration coefficient peculiar to the configuration of the particles of a given granular substance when measurement of particle size distribution is carried out on a mass of such particles the configuration of which is irregular, in order to obtain a better correspondence between observed results obtained by the method of the present invention as described above and the results obtained by the method of the prior art which generally uses sieves for the division of the mass of particles.

The average configuration coefficient for the correction of the particle size distribution according to the method of the present invention can be determined in the following way. First, a granular substance is fractioned to obtain particles having a known range of sizes by using a plurality of sieves and the projected area distribution of said fraction of particles is prepared experimentally by projecting the image of the particles from various directions. Then, assuming each particle of the fraction to have a configuration very near that of a rotational ellipsoid, a theoretical projected area distribution function of the fraction of the particles is prepared. Putting the observed distribution into the theoretical function, the average ratio of the length of the long axis to the length of the short axis of the particles is determined. The thus obtained value of the average ratio, based on the assumption that each particle of the assembly has the shape of a rotational ellipsoid, is defined as the average configuration coefficient of the particles of the overall mass of particles and the average coefficient is used for the correction of the particle size distribution experimentally determined by the method of the present invention.

The objects of the invention are further achieved by an apparatus for the measurement of particle size distribution by the method of the present invention. The apparatus is provided with an intermittent radiation means, a screen to be irradiated by said radiation means, a television camera which is arranged so as to view said screen while the particle of the granular substances move across the screen, and a device for processing the information on the projected images and which can calculate the projected area of each body of the mass by reading the output signals from the television camera which corresponds to the light and dark areas corresponding to the projected images.

The invention will be described in further detail with reference to the accompanying drawings.

DETAILED DESCRIPTION OF THE INVENTION

Figure 1:
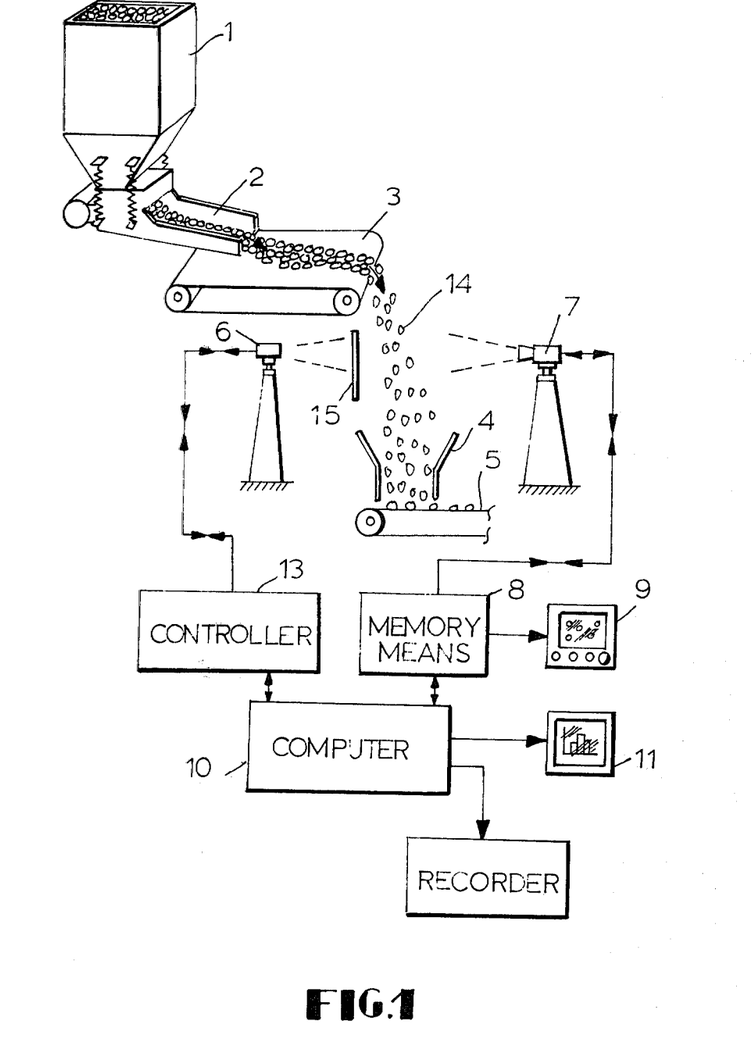
FIG. 1 is a schematic drawing showing an apparatus for carrying out the method of the present invention.

An example of the apparatus of the present invention which is used for the practice of the method of the present invention is shown in FIG. 1. A hopper 1 for the storage of a granular substance feeds the substance to a conventional take-out device 2 which operates to adjust the flow of the granular substance so that it is continuous and uniform. The take-out device 2 feeds the granular substance onto a first conveyor 3 which pours the substance through a hopper 4 onto a second conveyor 5. The granular substance, stored in the hopper 1 is taken out continuously, the amount of flow being regulated by said device 2 and then, after it is transported to the end of the first conveyor 3, it falls into the hopper 4 situated at an appropriately lower position than the end of the conveyor 3. The granular substance received in the second hopper 4 is discharged from the lower outlet of the hopper 4 onto the second conveyor 5 and is transported to the desired location.

On one side of the space through which the granular substance 14 is continuously freely falling from conveyor 3 to hopper 4, is provided a screen 15 which allows light to pass through with an appropriate intensity, and on the opposite side of the screen 15 from the zone is an intermittent radiation means 6 such as a stroboscope, for emitting bursts of radiation. On the opposite side of the falling material from the screen 15 is a television camera 7, the falling granular substance 14 falling between the camera 7 and the screen 15. A controller 13 is connected to the radiation means 6 which acts to turn the radiation means "On". A memory means 8 for receiving and storing images in the form of image signals is connected to the television camera 7 and receives signals corresponding to the images of the particles projected into the camera, recording the image of every particle in one unit consisting of one frame received by the television camera each time the radiation means is turned on. Both the controller 13 for the radiation means 6 and the memory means 8 are synchronously controlled by a computer 10 so as to make the background of the picture formed by the screen 15 light and make the particles of the granular substance 14 falling between the screen and the camera 7 dark in order to get a distinct contrast between the particles and the background. Thus the memory means 8 receives and stores distinct images of the particles from what appears to the camera 7 to be a static projected image of the particles and accumulates the images as analogic information or as digital information transformed into binary code from for dark and light, corresponding to the presence and absence of a projected image. A first monitor 9 is connected to the memory means 8 to display the static images of particles of the granular substance 14.

Figure 7:
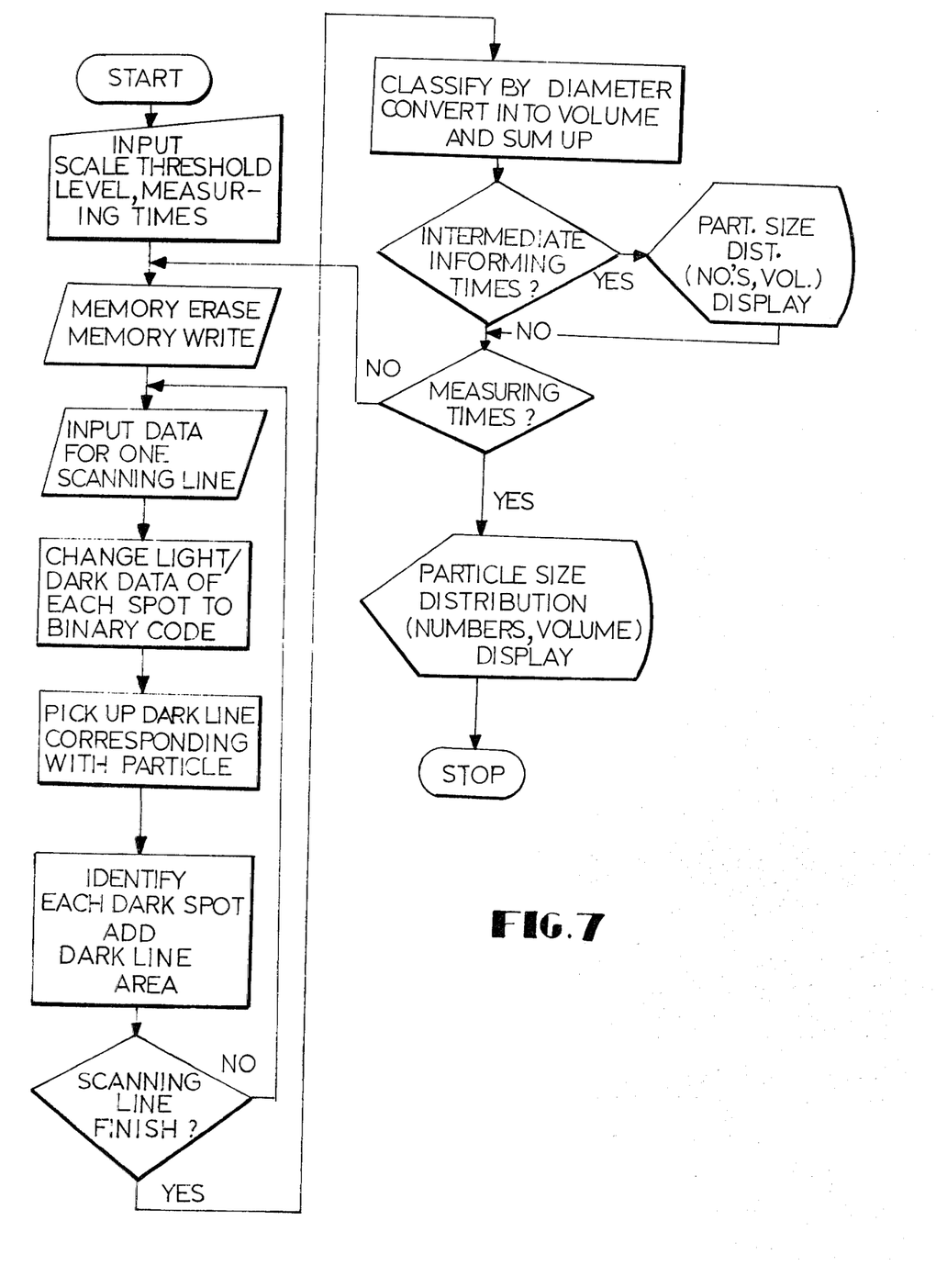
FIG. 7 is a flow-chart of software for measuring.

The computer 10 processes the data for all projected static images accumulated within the memory means 8, one by one by a conventional method to obtain the projected area of each particle of the granular substance 14 from the corresponding image, the diameter of the particle and the total number of particles. Moreover, using the values of the projected areas, the diameters and an input indicating the specific gravity of the particles of the granular substance 14, the computer 10 computes the weight of each particle and converts those data into the proportion of the overall weight for each given fraction of the fractions within a range of particle sizes indicated by software. A second monitor 11 is connected to the computer for displaying the particle size distribution computed as described above in the form of a histogram. A recorder 12 is connected to computer 10 to produce computed results in written form. A computer 10, for example, a computer known as HP-2100A (made by Hewlett Packard) may be used, and other computers may also be used. FIG. 7 shows an example of flow-chart of a program for measuring. The program for data transmitting and receiving with peripheral equipment is written in assembler language and the main program is written in FORTRAN language. The total volume of the program is about 8 K words.

Thus, the particle size distribution of the particles forming the mass of granular material 14 can be obtained using the apparatus shown in FIG. 1.

In practice, the method of measurement of particle size distribution as described above can be carried out in the following way. The flow of the falling granular substance 14 is adjusted by adjusting the operation of the take-out device 2 so that overlapping between particles hardly ever occurs when the flow 14 of falling particles is observed horizontally from the direction of the television camera. When such a condition is achieved, the feeding of the granular substance 14 to the first conveyor 3 from the hopper 1 through the take-out device 2 is continued without further adjusting the take-out device. The operation of the various measuring instruments for the computer 10 is then started and next the intermittent radiation means 6 and the memory 8 are started synchronously and accumulation of data corresponding to static projected images of particles of the granular substance 14 is carried out. The computer 10 is operated so as to process the thus obtained data for each frame, in order to compute the projected area of each particle of the granular substance 14, its diameter and the total number of the particles appearing in one frame. The particle size distribution of the particles of granular substance 14 can be obtained by converting this data into the weight of each fraction to the total weight. The result obtained by the computer 10 is displayed by the second monitor 11 as a histogram and recorded by the recorder 12.

During the processing of the information accumulated in the memory means 8, the computation of the particle diameter from a projected image is carried out assuming that the configuration of each particle is near a simple geometrical figure such as a sphere, a rotational ellipsoid or a cylinder. Furthermore, the particle size distribution of the particles in a mass of a granular substance can be obtained from projected images appearing only in one frame or the distribution can be determined as the mean value of the observed values obtained from a plurality of frames.

Furthermore, in the present invention, it is, of course, possible to put a screen between the television camera 7 and the flow 14 of the falling granular substance 14 and record the shadows of particles appearing on the screen by means of the television camera 7. Furthermore, for viewing the falling granular substance 14 in static projected images, the use of an intermittent radiation means is very effective as described above. Moreover, other means can be used. For example, it is possible to provide a shutter which is operated synchronously with the memory means 8 for projecting the images onto the television camera 7. Sampling of the projected image signals corresponding to one frame at any instant is also effective.

Furthermore, for eliminating the memory means 8 from the apparatus shown in FIG. 1, it is possible to transmit the output signal from the television camera 7 to the computer 10 through any conventional interface and operate the computer so as to process only information corresponding to one frame.

Furthermore, even if the particle size of the granular substance the particle size distribution of which is being measured is smaller than 1 mm, the apparatus shown in FIG. 1 can be used if a lens for magnifying the viewed image is attached to the television camera 10. Furthermore, if regulation of the flow of the falling granular substance only by the use of the take-out means 2 as described above becomes impossible due to conditions which must be met for the transportation of the granular substance as a raw material for a particular production process, the apparatus shown in FIG. 1 can be modified to provide a by-pass for the granular material in which the falling flow can be produced. As the television camera, there can be used not only the type of camera which is provided with an image tube but also cameras having a solid state device for reproducing pictures and having many picture elements.

The results of some experiments carried out according to the method of measurement of particle size distribution according to the present invention will now be described. When measurement was carried out on a granular substance the particles of which had a rather regular configuration near that of a sphere, the results of the measurement of particle size distribution based on the assumption that the configuration of each particle of the granular substance was a sphere satisfactorily coincided with the results obtained by the prior art method using sieves.

However, when measuring particle size distribution for a granular substance the particles of which had an irregular configuration, such as ore, coke breeze, etc., it was found that the particle size distribution obtained by the method of the present invention based on the assumption that each particle of the granular substance had a spherical configuration was somewhat different from that obtained by the method of the prior art. That is, the particle size distribution of a mass of irregular particles obtained by the method of the present invention assuming a spherical configuration for each particle shifts slightly but clearly to the small size end of the range of particle sizes as compared with the distribution obtained by the prior art method using sieves. This may be attributable to the fact that in the method of the present invention, these irregular particles have a tendency to fall with their short axis horizontal. For this reason, a method of correction to take into account the irregularities of the shape of the particles have been developed as one of the characteristics of the present invention. Thus, the observed particle size distribution after the correction by the method of the present invention satisfactorily concides with particle size distribution obtained by fractionation using sieves. The correction is carried out by assuming that the configuration of the irregular particles is a rotational ellipsoid.

Coefficients to indicate the configuration of a particle of a granular substance, namely a volume configuration coefficient $\overline{\Phi}_V$ and a surface configuration coefficient $\overline{\Phi}_A$ are well known. If the average diameter of the particles of a mass of a granular substance is represented by dp, the average volume by V and the average surface area by A, then $\overline{\Phi}V$ and $\overline{\Phi}A$ can be defined by the equations (1) and (2).

$$V = \overline{\Phi}_V d p^3 \quad (1)$$

$$A = \overline{\Phi}_A d p^2 \quad (2)$$

As described above, in the present invention, the configuration of each irregular particle in a mass of particles is assumed to be a rotational ellipsoid. Of course, this assumption is not itself a new one. However, this assumption has a large influence in the method of the present invention, as will be clearly understood from the explanation given hereinafter. In the present invention, the average configuration coefficient is theoretically determined for correcting the particle size distribution to take into account the fact that the shape of the particles of the granular substance is irregular. Using an experimental observation based on the assumption described above, the average configuration coefficient is defined as the average value of the ratio of the long axis to the short axis of each particle contained in a mass of irregular particles which are assumed to have a configuration very near to a rotational ellipsoid as described above and the coefficient corresponds to the definitions $\overline{\Phi}_V$ and $\overline{\Phi}_A$.

Figure 2:
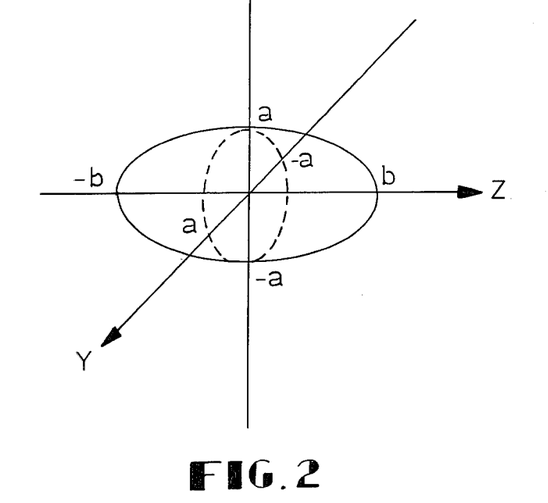
FIG. 2 is a diagram showing the dimensional relationships of a rotational ellipsoid which can be assumed to have a configuration very similar to each particle of a granular substance the particle size distribution of which is to be measured by the method of the present invention.

FIG. 2 shows a rotational ellipsoid, the short axis of which is represented as a and the long axis of which is represented as b, which is assumed to be the configuration of each irregular particle of the mass of particles being analyzed. The rotational ellpsoid can be represented by the following mathematical equation if the three axes x, y and z are as shown in FIG. 2.

$$\frac{x^2}{a^2} + \frac{y^2}{a^2} + \frac{z^2}{b^2} = 1 \qquad (3)$$

The ratio r of the long axis of the short axis of the particle, which is the configurational coefficient of the particle, is given by:

$$r = b/a \qquad (4)$$

Figure 3:
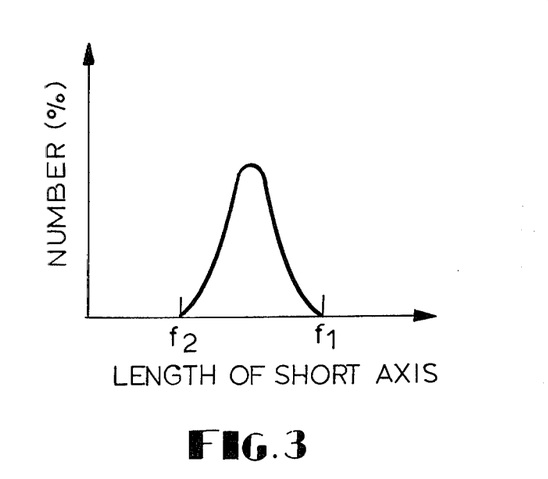
FIG. 3 is a diagram showing the distribution of the lengths of the short axis of a classified fraction of particles from among the total number of particles in a mass of particles and assuming each particle is a rotational ellipsoid such as shown in FIG. 2.

In determining the average configuration coefficient for a particular granular material the particle size distribution of which is to be measured, a sample of the material is first separated to obtain a class of particles by using two kinds of sieves the size of the meshes of which are $f_1$ and $f_2$ (here, $f_1 > f_2$), in order to remove larger and smaller particles. That is, the sample of the granular material is separated using the sieve with mesh size $f_1$ to remove particles the short axis of which is larger than $f_1$. The particles remaining are again separated using the sieve with mesh size $f_2$ to remove particles the short axis of which is smaller than $f_2$. The thus obtained fraction is a mass of particles with the length of the short axis between $f_2$ and $f_1$, wherein the distribution of the lengths of the short axis in the mass of particles can be reasonably assumed to be a normal distribution as shown in FIG. 3.

The projected area distribution Fex(S) of the thus classified particles is experimentally determined by observing the projected areas and counting the number of particles more than a score of times as the particles are falling from the conveyor 3 of the apparatus of FIG. 1.

In the determination P(a,r,S) is defined as a projected area distribution function of a rotational ellipsoid which can be represented mathematically by the equation (3), when the projection is carried out from $4\pi$ directions, that is the projection is carried out from random directions. In this function, r is the ratio of the long axis to the short axis as shown in equation (4) and S is the projected area of the particle.

Furthermore, since it is reasonable to consider that it is possible for such a particle having the shape of a rotational ellipsoid to pass through a sieve having a mesh size larger than the short axis of the particle and it is impossible for such a particle to pass through a sieve having a mesh size smaller than the short axis, the distribution function of the mass of such particles, G(x), represented in the number of particles, is believed to be a normal distribution, $$G(x) = \frac{1}{\sqrt{2\pi}\sigma} e^{-\frac{(x-x_0)^2}{2\sigma^2}} \qquad (5)$$

wherein $\sigma_0$ and $\sigma$ are arbitrary, positive constants.

Theoretically, the projected area distribution function F (S) of such a mass consisting of rotational ellipsoid particles corresponding to a normal distribution (5) is given by the equation (6).

$$F(S) = \int_{f_2}^{f_1} P(D,r',S) \cdot G(D) \cdot dD \qquad (6)$$

Wherein P, G and S are as described above, D is the length of the short axis of each particle and r' is the average value of the ratio of the long axis to the short axis of each particle contained in the mass. Using equation (6) and setting it equal to the experimentally obtained result Fex(S), the value of r' can be determined. This value of r' is the average configuration coefficient for the particles of the mass of particles assumed to be rotational ellipsoids according to the method of the present invention.

Figure 4A:
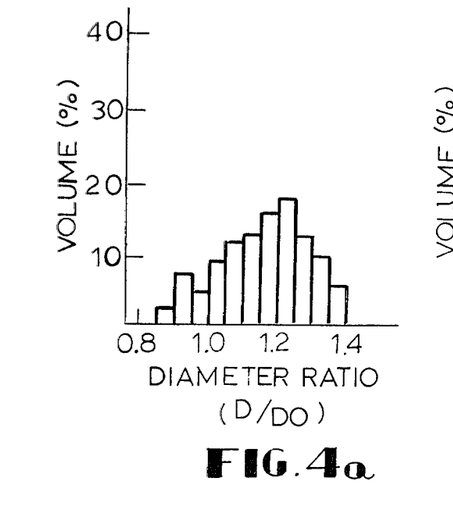
FIG. 4(A) is a histogram showing the particle size distribution of a mass of ore particles obtained experimentally by the method of the present invention assuming the configuration of each particle is spherical.
Figure 4B:
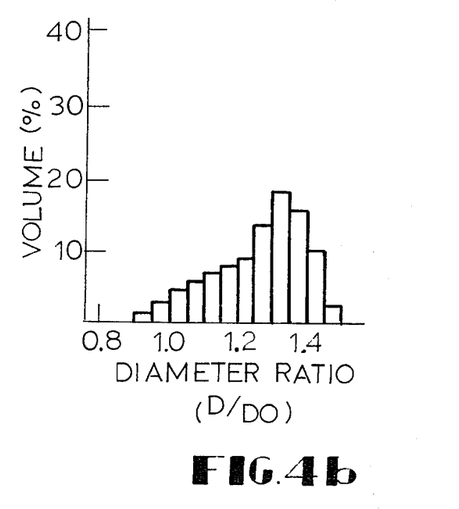
FIG. 4(B) is a histogram showing the theoretical particle size distribution of the mass of ore particles used in obtaining the histogram of FIG. 4(A), after performing a correction using an average configurational coefficient.
Figure 5A:
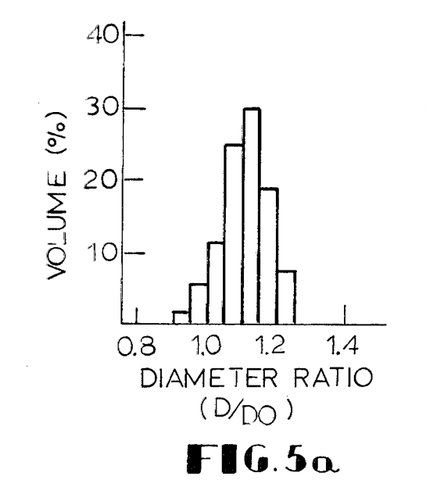
FIG. 5(A) is a histogram showing the particle size distribution of a mass of sintered ore particles obtained experimentally by the method of the present invention assuming the configuration of each particle is spherical.
Figure 5B:
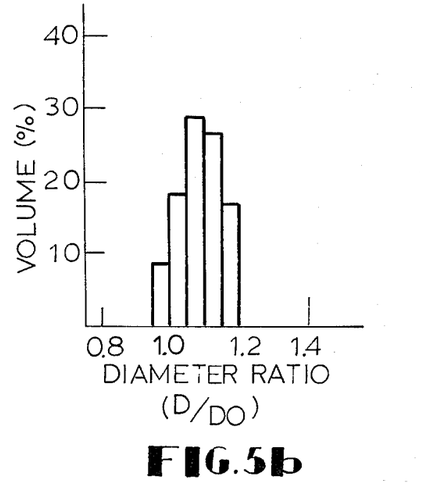
FIG. 5(B) is a histogram showing the theoretical particle size distribution of the mass of sintered ore particles used in obtaining the histogram of FIG. 5(A), after performing a correction using an average configurational coefficient.
Figure 6:
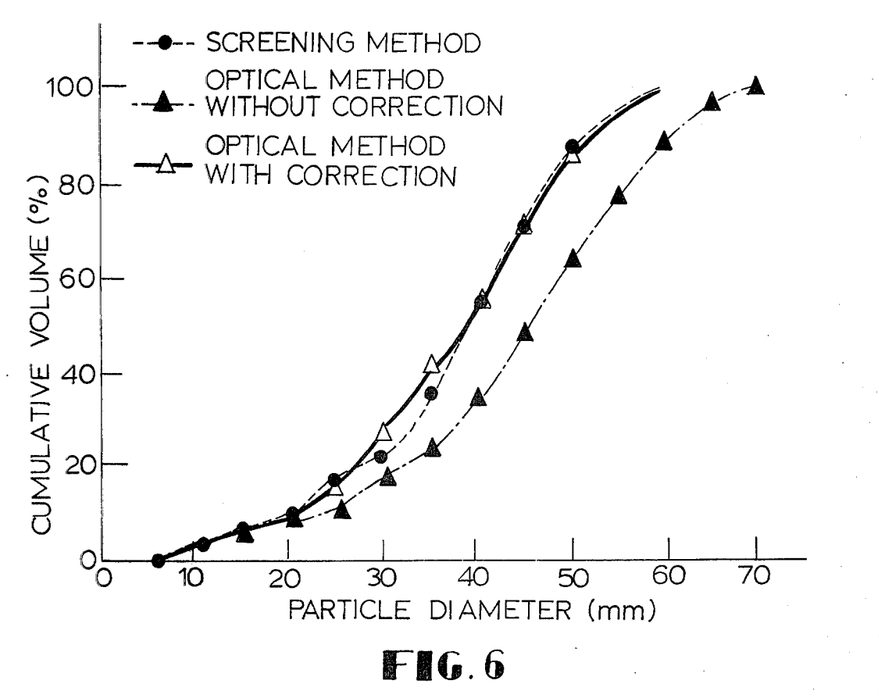
FIG. 6 is a graph showing a comparison of the data obtained by a screening method, an optical method without correction and an optical method with correction.

The practice and effectiveness of the method of correcting by using the average configuration coefficient will be shown by reference to FIGS. 4(A) and (B), FIGS. 5(A) and (B) and FIG. 6. FIG. 4(A) shows the particle size distribution of fractions of a sample mass of particles of ore obtained by observation of the projected area distribution of the sample mass of particles with the method of this invention and assuming each particle had a configuration very near to a sphere. Said sample mass of ore particles were prepared by removing larger particles by sieving with a sieve having a mesh size of 35 mm and removing smaller particles by sieving with a sieve having a mesh size of 30 mm. In the figures, the abscissae show the diameter ratio of particles, that is the ratio of the length D of the short axis which is $$D = 2 \times \sqrt{\frac{A}{\pi}}$$

of a rotational ellipsoid to the average length $D_o$ of the short axis (in FIGS. 4(A) and (B) $D_o = 32.5$ mm) of the particles of the separated fractions, and the ordinates show the percent of the volume of the mass of particles having a given diameter ratio. FIG. 4(B) shows the theoretical particle size distribution of said sample mass, which is obtained by equation (6) with $r' = 1.9$.

Before the measurement of the whole mass the particle size distribution of which is to be measured, the particle size distribution of the sample mass obtained by sieving, for example with two sieves whose mesher are $f_1 = 35$ mm and $f_2 = 30$ mm respectively as described above, is measured by an optical method or the method of this invention assuming each particle has a configuration very near to a sphere, and by a screening method or a prior method. The result by the former method is shown in FIG. 4(A) and the result by the latter method resembles FIG. 4(B). The difference between said results is caused by the assumption that each particle has a configuration very near to a sphere, because the configuration of an ore particle is irregular.

Then, assuming the configuration is near to a rotational ellipsoid, the most suitable value of r' is searched for with the aid of equation (6), wherein said value of r' makes the theoretical distribution based on the result of FIG. 4(A) coincide with the result by the screening method. In the case described above, the value of r' was 1.9.

As described above, plural values of r' corresponding to various sample masses are obtained. After that, the distribution of said whole mass is measured by the apparatus of this invention and the result is corrected by said value of r'.

FIG. 6 shows the cumulative volume percent of mass of ore in relation to the particle diameter, wherein black circlets, black triangles and white triangles show the results by the screening method, the optical method without correction and the optical method with correction, respectively. As shown in FIG. 6, the result of the present method with this correction coincides with the one by the prior screening method very well.

FIGS. 5(A) and (B) correspond to FIGS. 4(A) and (B) respectively, wherein the mass of particles is sintered ore, and the sample mass is separated by two sieves having a mesh size of 50 mm and 45 mm respectively. The value of r' in FIG. 5(B) is 1.3. Thus the effectiveness of the correction in the method of the present invention has been proved. Therefore, it is concluded that before carrying out a measurement for the determination of the particle size distribution of a granular substance by the method of the present invention using an apparatus such as shown in FIG. 1, it is highly desirable to determine the average configuration coefficient, that is, the average ratio r' of the length of the long axis to the length of the short axis (as described above) and to apply the thus obtained coefficient to the calculation of the volume or weight in the computation of the particle size distribution. By the use of this coefficient, it becomes possible to obtain a result which satisfactorily corresponds with the results obtained by the prior art fractioning method using sieves.

As described above, by the use of the present invention, it becomes possible to obtain accurate information on the particle size distribution of granular substances during their tranportation, both continuously and rapidly in real time and without removing a sample from the transported material. This makes it possible to utilize the results of such a measurement as information to carry out feedback control of particle size distribution for management of the production process in which the granulated substance is used. Moreover, it can be pointed out that the method of measurement of the present invention can be applied to various granular substances without any limitation as to particle size and shape and, when the shape of the particles is irregular, a correction can be made in order to obtain a particle size distribution very similar to that obtained by the prior art fractioning method using sieves.

Since the apparatus for carrying out the method of the present invention is not a large one, but is rather compact, it is possible to provide the apparatus in an appropriate space along an existing conveyor line. Therefore, the apparatus is very practical. For example, by the use of the present invention, it becomes possible to manage the operation of a blast furnace with high accuracy, or to carry out an effective quality control of raw materials or products consisting of granular substances, rapidly and accurately. Thus, the invention can play an important role in various industrial fields.

What is claimed is:

1. A method of determining particle size distribution of particles in a mass of a granular substance, comprising:

causing the mass of the granular substance to fall in a stream of separate particles through a predetermined distance;

producing a static image of the projected areas of the falling particles of the granular substance by providing a light transmitting screen along one side of the falling stream of particles, intermittently lighting said screen for brief periods of time for producing images of the particles in the stream of particles when the screen is viewed from a position laterally of the stream, the periods of the illumination being sufficiently brief to cause the images to appear to be motionless, and televising the images of the particles at at least one period of lighting of the screen, and measuring the projected areas of the images by utilizing the video signal of the televised instantaneous image of the falling stream of particles as the source of information of the number of particles and the areas of the respective particles, the images of which have been televised; and, from the projected areas and assuming the average shape of the particles to be substantially a rotational ellipsoid, calculating the sizes of the individual particles and the distribution of the sizes of the particles in the mass.

2. A method as claimed in claim 1 in which said screen is lighted from the side opposite the side along which the falling stream of particles is falling, and said televising is from the side of the falling stream of particles on the opposite side thereof from the screen.

3. An apparatus for determining particle size distribution of particles in a mass of a granular substance, comprising:

means for causing a mass of the granular substance to fall in a stream of separate particles through a predetermined distance;

a light transmitting screen along one side of the falling stream of particles;

a radiation means for irradiating said screen with an intermittent radiation for producing images of the particles in the stream of particles;

a television camera directed toward said screen for televising the images at at least one instant of irradiation of said screen;

and means connected to said television camera for processing the video output signal of said television camera for determining the projected areas of said particles and, from said projected areas and an assumption that the shape of the particles is substantially a rotational ellipsoid calculating the distribution of the sizes of the particles in the mass.

4. An apparatus for determining the particle size distribution of particles in a mass of a granular substance and falling in a stream of separate particles through a predetermined distance, said apparatus comprising;

a light transmitting screen along one side of the falling stream of particles;

a radiation means for irradiating said screen with an intermittent radiation for producing images of the particles in the stream of particles;

a television camera directed toward said screen for televising the images at at least one instant of irradiation of said screen;

and means connected to said television camera for processing the video output signal of said television camera for determining the projected areas of said particles and, from said projected areas and an assumption that the shape of the particles is substantially a rotational ellipsoid, calculating the distribution of the sizes of the particles in the mass.

5. An apparatus as claimed in claim 4 in which said radiation means is located on the side of said screen opposite the falling stream of particles and said television camera is on the opposite side of the stream of particles from said screen.

6. A method of determining the size distribution of particles in a mass of granular substance, comprising:

causing the mass of the granular substance to fall in a stream of separate particles through a predetermined distance;

producing at least one static image of the projected areas of the falling particles of granular substance at one instant during the fall of the particles by a television camera;

measuring the projected areas of the particles and counting the number of particles by utilizing the video signal of the televised image as the source of information;

determining the average configuration coefficient for the particles of the mass by sieving a sample of the mass of particles for obtaining a group of particles having known maximum and minimum particle sizes, causing the thus obtained group to fall in a stream of separate particles and producing a static image of the projected areas of the falling particles of said group at one instant during the fall of the particles by a television camera, and measuring the projected areas and the projected area distribution of the particles of said group by utilizing the video signal of the televised image as the source of information, and substituting the thus experimentally determined projected area distribution in the theoretical expression for projected area distribution, which theoretical expression includes an unknown average configuration coefficient and determining a value for said average configuration coefficient from said expression which contains the experimentally determined projected area distribution; and from the projected area of the particles of the falling mass of particles and the thus determined value of the average configuration coefficient, calculating the sizes of the individual particles in the mass and from them the distribution of the sizes of the particles in the mass.

* * * * *